(12) United States Patent
Cao et al.

(10) Patent No.: US 9,357,976 B2
(45) Date of Patent: Jun. 7, 2016

(54) SYSTEM AND METHOD OF NOISE DELETION IN COMPUTED TOMOGRAPHY

(71) Applicant: General Electric Company, Schenectady, NY (US)

(72) Inventors: Guangzhi Cao, Waukesha, WI (US); Jiahua Fan, Waukesha, WI (US); Edgar Chino, Waukesha, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 226 days.

(21) Appl. No.: 14/062,207

(22) Filed: Oct. 24, 2013

(65) Prior Publication Data
US 2015/0117596 A1    Apr. 30, 2015

(51) Int. Cl.
*A61B 6/00* (2006.01)
*A61B 6/03* (2006.01)
*G06T 11/00* (2006.01)

(52) U.S. Cl.
CPC .............. *A61B 6/5264* (2013.01); *A61B 6/032* (2013.01); *A61B 6/5258* (2013.01); *G06T 11/006* (2013.01); *G06T 11/008* (2013.01); *A61B 6/4291* (2013.01); *G06T 2211/424* (2013.01)

(58) Field of Classification Search
CPC ......... A61B 6/032; A61B 6/5205; A61B 6/03
USPC ................................ 378/4–20, 901; 382/131
See application file for complete search history.

(56) References Cited

U.S. PATENT DOCUMENTS

| | | |
|---|---|---|
| 2012/0039440 A1 | 2/2012 | Fan et al. |
| 2012/0183108 A1 | 7/2012 | Narayanan et al. |
| 2013/0170609 A1 | 7/2013 | Nett et al. |
| 2013/0202080 A1* | 8/2013 | Yu et al. .......................... 378/19 |
| 2013/0343623 A1 | 12/2013 | Fan et al. |
| 2014/0270454 A1* | 9/2014 | Chen et al. .................... 382/132 |

OTHER PUBLICATIONS

Milanfar, Peyman, "A Tour of Modern Image Filtering"; published in IEEE Signal Processing Magazine Jan. 2013.

* cited by examiner

*Primary Examiner* — Hoon Song
(74) *Attorney, Agent, or Firm* — Fletcher Yoder, P.C.

(57) ABSTRACT

An imaging system includes a computer programmed to reconstruct original CT projection data, estimate noise in image space, forward project the image noise estimate to generate an initial projection noise estimate, modify the initial projection noise estimate using a statistical property of noise in projection space, remove noise in the original CT projection data by subtracting the modified noise estimate therefrom to generate noise-removed projection data, and reconstruct a final image based on the noise-removed projection data.

20 Claims, 6 Drawing Sheets

SYSTEM AND METHOD OF NOISE DELETION IN COMPUTED TOMOGRAPHY

BACKGROUND

This disclosure relates generally to diagnostic imaging and, more particularly, to an apparatus and method of de-noising and restoring signals in computed tomography (CT) imaging system.

Typically, in computed tomography (CT) imaging systems, an x-ray source emits a fan or cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom. Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are transmitted to the data processing system for image reconstruction. Imaging data may be obtained using x-rays that are generated at a single polychromatic energy. However, some systems may obtain multi-energy images that provide additional information for generating images.

During scanning to acquire projection data, it is generally desirable to reduce x-ray dose received by the subject, thus protocols have been developed that reduce x-ray tube power and patient exposure during image data acquisition. Also, gantry speeds in CT imaging generally continue to increase over time, in an effort to capture images in a shorter time period to reduce motion artifacts. Thus, as dose is reduced and as gantry speed increases, the general trend is to reconstruct images using lower amounts of photons passing through the image volume, resulting in a reduced signal-to-noise ratio (SNR). As such, the effect of statistical noise has thereby increased, resulting in an increased propensity for noise-induced artifacts. Thus, there is a need to account for statistical noise in CT scanners.

To account for noise, signal restoration has traditionally been performed using closed-form or iterative solutions that are essentially based on neighbor pixels. For instance, in a known closed-form solution, signal restoration is performed through a weighted average of its neighbor pixels, using linear or non-linear noise filtering or smoothing algorithms such as Gaussian smoothing, bi-lateral filtering, and the like. In a known iterative solution, noise is estimated using an iterative "cost-optimization" approach in which the noise is iteratively estimated based on the surrounding pixels.

A disadvantage of such methods, however, is that while noise is averaged out, the contrast among neighboring pixels is also averaged out. Thus, when these known methods are applied to signals having a low SNR, a blurred version of the original signal can result.

Therefore, it would be desirable to improve the estimate of statistical noise without blurring the original signal.

BRIEF DESCRIPTION

Embodiments are directed toward a method and apparatus of de-noising and restoring signals in a computed tomography (CT) system in medical imaging.

According to one aspect, an imaging system includes a computer programmed to reconstruct original CT projection data, estimate noise in image space, forward project the image noise estimate to generate an initial projection noise estimate, modify the initial projection noise estimate using a statistical property of noise in projection space, remove noise in the original CT projection data by subtracting the modified noise estimate therefrom to generate noise-removed projection data, and reconstruct a final image based on the noise-removed projection data.

According to another aspect, a method of de-noising CT imaging data includes estimating noise in image space from reconstructed originally acquired CT projection data, modifying the estimated noise in projection space using a statistical property of noise in projection space, subtracting noise from the originally acquired CT projection data using the modified estimation of the noise to generate noise-removed projection data, and reconstructing a final image using the noise-removed projection data.

According to yet another aspect, a non-transitory computer readable storage medium having stored thereon a computer program comprising instructions, which, when executed by a computer, cause the computer to reconstruct originally acquired CT projection data, estimate noise in image space in the reconstructed data, forward project the image noise estimate to generate an initial projection noise estimate, modify the initial projection noise estimate using a statistical property of noise in projection space, remove noise in the originally acquired CT projection data by subtracting the modified noise estimate therefrom to generate noise-removed projection data, and reconstruct a final image based on the noise-removed projection data.

Various other features and advantages will be made apparent from the following detailed description and the drawings.

DETAILED DESCRIPTION

The operating environment of disclosed embodiments is described with respect to a sixty-four-slice computed tomography (CT) system. However, it will be appreciated by those skilled in the art that disclosed embodiments are equally applicable for use with other multi-slice configurations, or other imaging systems in general, such as an x-ray system on a c-arm or a micro-CT system, as examples. Moreover, disclosed embodiments will be described with respect to the detection and conversion of x-rays. However, one skilled in the art will further appreciate that embodiments are equally applicable for the detection and conversion of other high frequency electromagnetic energy. Disclosed embodiments will be described with respect to a "third generation" CT scanner, but is equally applicable with other CT systems as well as vascular and surgical C-arm systems and other x-ray tomography systems.

Figure 1:
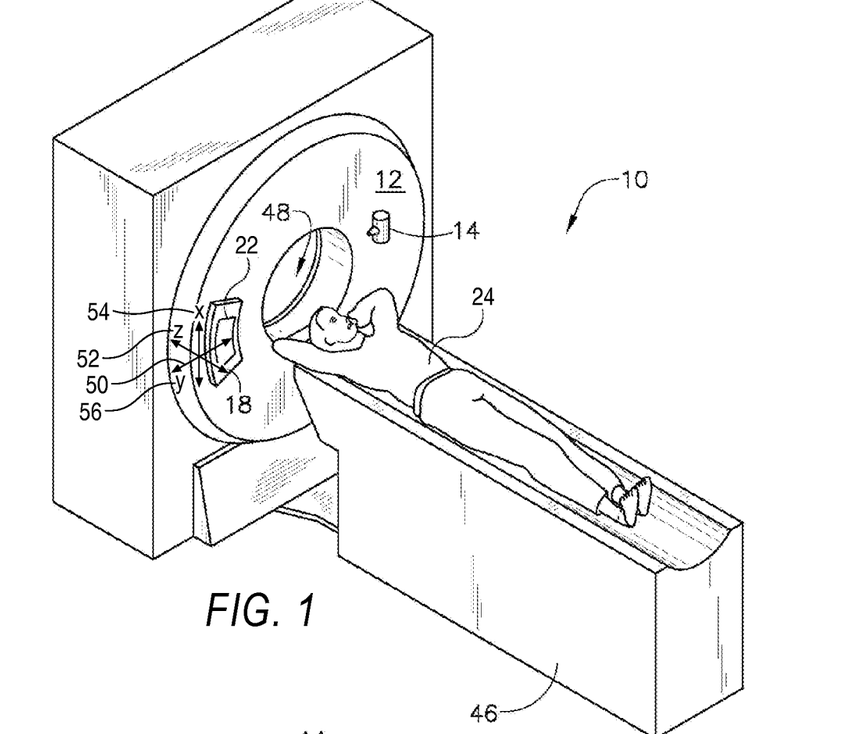
FIG. 1 is a pictorial view of a CT imaging system.
Figure 2:
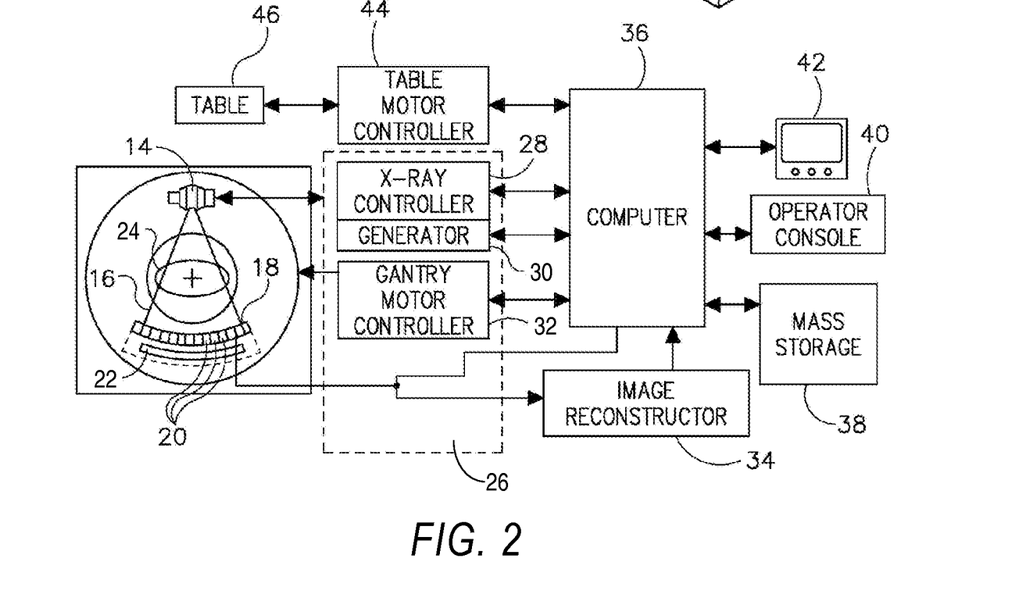
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector assembly or collimator 18 on the opposite side of the gantry 12. X-ray source 14 includes either a stationary target or a rotating target. Detector assembly 18 is formed by a plurality of detectors 20 and data acquisition systems (DAS) 22. The plurality of detectors 20 sense the projected x-rays that pass through a medical patient 24, and DAS 22 converts the data to digital signals for subsequent processing. Each detector 20 produces an analog electrical signal that represents the intensity of an impinging x-ray beam and hence the attenuated beam as it passes through patient 24. During a scan to acquire x-ray projection data, gantry 12 and the components mounted thereon rotate about a center of rotation 26.

Rotation of gantry 12 and the operation of x-ray source 14 are governed by a control mechanism 26 of CT system 10. Control mechanism 26 includes an x-ray controller 28 and generator 30 that provides power and timing signals to x-ray source 14 and a gantry motor controller 32 that controls the rotational speed and position of gantry 12. An image reconstructor 34 receives sampled and digitized x-ray data from DAS 22 and performs high speed image reconstruction. The reconstructed image is applied as an input to a computer 36 which stores the image in a mass storage device 38.

Computer 36 also receives commands and scanning parameters from an operator via an operator console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 22, x-ray controller 28, and gantry motor controller 30. In addition, computer 36 operates a table motor controller 44 which controls a motorized table 46 to position patient 24 and gantry 12. Particularly, table 46 moves patients 22 through a gantry opening 48 in whole or in part. A coordinate system 50 for detector assembly 18 defines a patient or Z-axis 52 along which patient 24 is moved in and out of opening 48, a gantry circumferential or X-axis 54 along which detector assembly 18 passes, and a Y-axis 56 that passes along a direction from a focal spot of x-ray tube 14 to detector assembly 18.

X-ray source 14, in accordance with present embodiments, is configured to emit x-ray beam 16 at one or more energies. For example, x-ray source 16 may be configured to switch between relatively low energy polychromatic emission spectra (e.g., at approximately 80 kVp) and relatively high energy polychromatic emission spectra (e.g., at approximately 140 kVp). As will be appreciated, x-ray source 14 may also be operated so as to emit x-rays at more than two different energies. Similarly, x-ray source 14 may emit at polychromatic spectra localized around energy levels (i.e., kVp ranges) other than those listed herein (e.g., 100 kVP, 120 kVP, etc.). Selection of the respective energy levels for emission may be based, at least in part, on the anatomy being imaged.

In some embodiments x-ray controller 28 may be configured to selectively activate x-ray source 14 such that tubes or emitters at different locations within system 10 may be operated in synchrony with one another or independent of one another. In certain embodiments discussed herein, the x-ray controller 28 may be configured to provide fast-kVp switching of x-ray source 14 so as to rapidly switch source 14 to emit X-rays at the respective polychromatic energy spectra in succession during an image acquisition session. For example, in a dual-energy imaging context, x-ray controller 28 may operate x-ray source 14 so that x-ray source 14 alternately emits x-rays at the two polychromatic energy spectra of interest, such that adjacent projections are acquired at different energies (i.e., a first projection is acquired at high energy, the second projection is acquired at low energy, the third projection is acquired at high energy, and so forth). In one such implementation, fast-kVp switching operation performed by x-ray controller 28 yields temporally registered projection data. In some embodiments, other modes of data acquisition and processing may be utilized. For example, a low pitch helical mode, rotate-rotate axial mode, N×M mode (e.g., N low-kVp views and M high-kVP views) may be utilized to acquire dual-energy datasets.

Techniques to obtain energy sensitive measurements include: (1) scan with two distinctive energy spectra and (2) detect photon energy according to energy deposition in the detector. Such measurements provide energy discrimination and material characterization, and may be used to generate reconstructed images using a base material decomposition (BMD) algorithm. A conventional BMD algorithm is based on the concept that, in an energy region for medical CT, the x-ray attenuation of any given material can be represented by a proper density mix of two materials with distinct x-ray attenuation properties, referred to as the base or basis materials. The BMD algorithm computes two CT images that represent the equivalent density of one of the base materials based on the measured projections at high and low x-ray photon energy spectra, respectively.

Thus, CT image data is obtained that may be from a single or a dual energy application. CT reconstruction is generally a two-step process. The patient is placed on the scanner and an x-ray beam is caused to rotate about the patient, either in a helical or an axial operation. Detectors measure the pattern of radiation (projection) transmitted through the patient. Image reconstruction from the projections is performed using a filtered backprojection (FBP).

Figure 3:
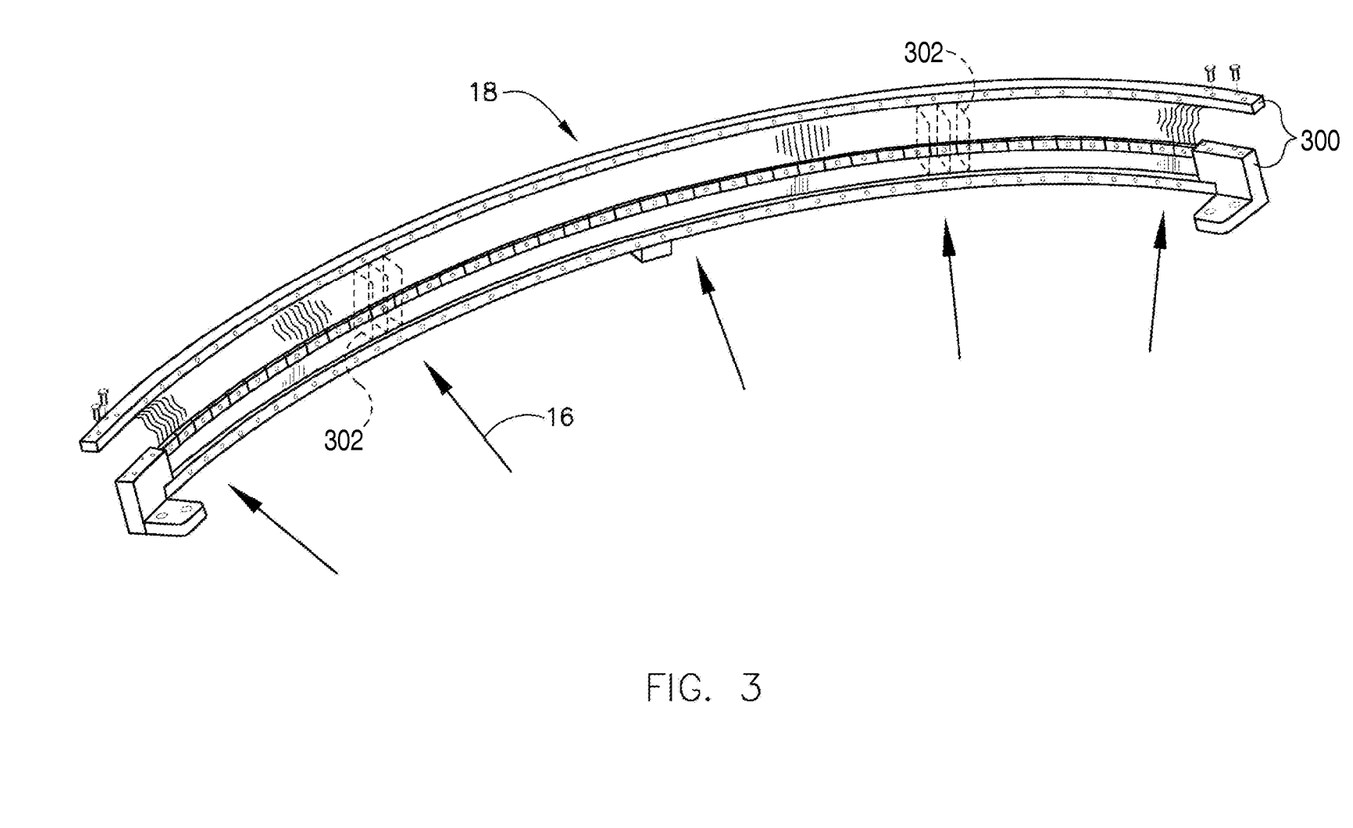
FIG. 3 is a perspective view of one embodiment of a CT system detector array.

As shown in FIG. 3, detector assembly 18 includes rails 300 having collimating blades or plates 302 placed therebetween. Plates 302 are positioned to collimate x-rays 16 before such beams impinge upon, for instance, detector 20 of FIG. 4 positioned on detector assembly 18. In one embodiment, detector assembly 18 includes fifty-seven detectors 20, each detector 20 having an array size of 64×16 of pixel elements 400. As a result, detector assembly 18 has sixty-four rows and nine hundred twelve columns (16×57 detectors) which allows sixty-four simultaneous slices of data to be collected with each rotation of gantry 12.

Figure 4:
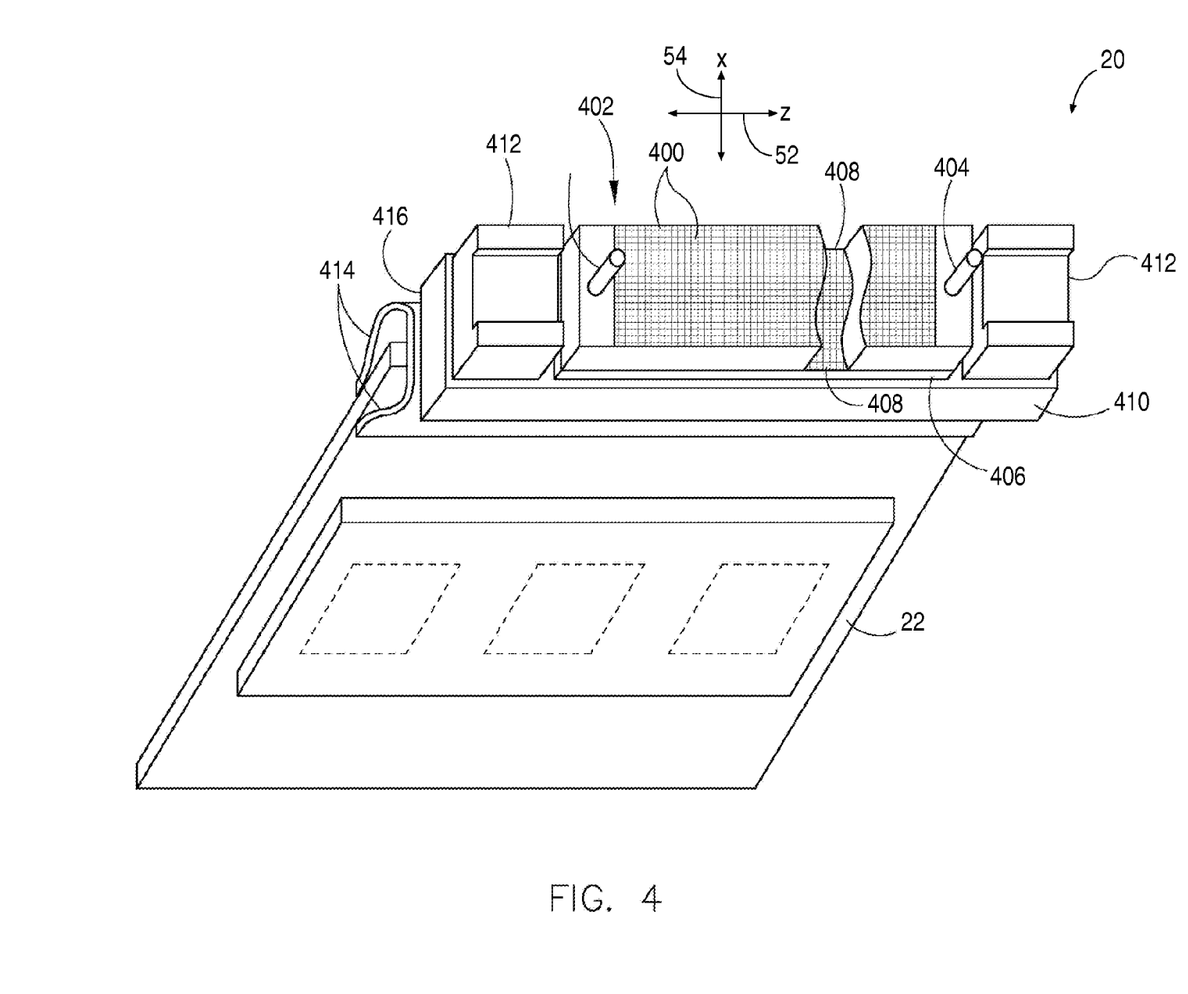
FIG. 4 is a perspective view of one embodiment of a detector.

Referring to FIG. 4, detector 20 includes DAS 22, with each detector 20 including a number of detector elements 400 arranged in pack 402. Detectors 20 include pins 404 positioned within pack 402 relative to detector elements 400. Pack 402 is positioned on a backlit diode array 406 having a plurality of diodes 408. Backlit diode array 406 is in turn positioned on multi-layer substrate 410. Spacers 412 are positioned on multi-layer substrate 410. Detector elements 400 are optically coupled to backlit diode array 406, and backlit diode array 406 is in turn electrically coupled to multi-layer substrate 410. Flex circuits 414 are attached to face 416 of multi-layer substrate 410 and to DAS 22. Detectors 20 are positioned within detector assembly 18 by use of pins 404.

According to disclosed embodiments, an underlying signal is restored from a contaminated measurement. Let x be an n-dimensional vector that represents the true signal that is desired to be measured, and y is an n-dimensional vector that is actually measured. Generally, the signal measurement process can be modeled as:

$$y = x + w;$$ Equation (1);

where w is an n-dimensional independent additive noise vector with zero mean. The objective of signal restoration is to compute a good estimate of the true signal x based on the measurement y.

Traditionally, signal restoration has generally been performed through weighted average of its neighborhood pixels, i.e.:

$$\hat{x}_i = \sum_{j \in N_i} a_j y_j;$$ Equation (2);

where $N_i$ represents the neighborhood of pixel i. Many of the linear and non-linear noise filtering/smoothing algorithms belong to this category, such as Gaussian smoothing, bi-lateral filtering and more recently developed non-local mean where the definition of the neighborhood N is broadened. The disadvantage of this type of method is, as summarized above, while the noise is averaged out, the contrast among the neighboring pixels is also unavoidably averaged out. Therefore, when this type of method is applied aggressively on signals with a low SNR, a blurred version of the original signal generally results.

Figure 5:
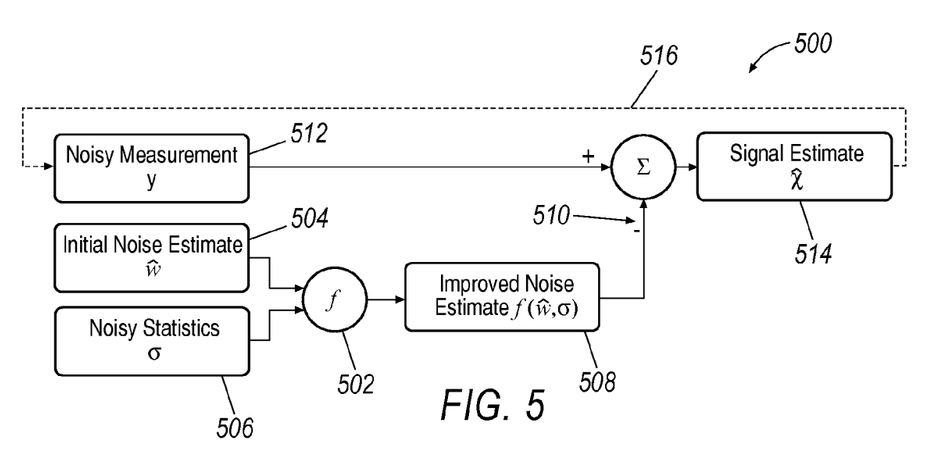
FIG. 5 is a block representation of de-noising and restoring a signal.

In this disclosure, a method is disclosed herein that is based on direct removal of the noise instead of averaging/smoothing. Let σ be the known standard deviation of w and ŵ is an initial estimate of the noise. The disclosed method for computing the restored signal can be formulated as:

$$\hat{x} = y - f(\hat{w}, \sigma) = x + W - f(\hat{w}, \sigma);$$ Equation (3);

where $f(\hat{w}, \sigma)$ is a non-linear operator that modifies the initial noise estimate ŵ based on the statistical property of w. It can be seen that if $|f(\hat{w}, \sigma)| < |w|$ with the same sign and $f(\hat{w}, \sigma)$ are obtained independently, $\hat{x}$ is a noise reduced estimate of y and the contrast would remain unchanged between the neighboring pixels. Therefore, $f(\hat{w}, \sigma)$ generally needs to be a non-decreasing function of both ŵ and a. In FIG. 5, a diagram of the proposed approach is provided. Note that the proposed approach can be applied iteratively as indicated by the dotted line. In practice, however, in one embodiment, one iteration is sufficient.

Thus, referring to FIG. 5, a symbolic representation 500 of Equation 3 is illustrated in which function $f$ is derived at block 502 based on initial noise estimate ŵ at block 504 and based on noisy statistics, at block 506. $f(\hat{w}, \sigma)$ is an improved noise estimate, at block 508, which is subtracted 510 from a noisy measurement y, from block 512, resulting in a signal estimate $\hat{X}$, at block 514. As stated, the process may be iterated 516 to further improve estimate $\hat{X}$.

Theoretical support for the above-described discussion is provided herein. For independent noise, one example of the function $f$ can be given as:

$$f(\hat{w}_i, \sigma_i) = \begin{cases} \hat{w}_i & \text{if } |\hat{w}_i| \leq \alpha \cdot \sigma_i \\ \text{sign}(\hat{w}_i) \cdot \alpha \sigma_i & \text{Otherwise} \end{cases};$$ Equation (4);

where α is effectively a regularization parameter of a positive value. It can be seen that the hard thresholding function $f$ modifies the initial noise estimate $\hat{w}_i$ and makes it better follow the known noise distribution. The thresholding function is based, in the above example, on A) the initial estimate of noise, and B) noise statistics, such as standard deviation.

The function $f(\hat{w}, \sigma)$ is a solution to a cost optimization problem that does bear a theoretical explanation, i.e., $f(\hat{w}, \sigma)$ can be viewed as a constrained maximum likelihood estimator (MLE) of the noise w. Specifically, let $\Lambda = \text{diag}(1/\sigma_1, 1/\sigma_2, \ldots, 1/\sigma_n)$. The function $f(\hat{w}, \sigma)$ in Eqn. (4) is the solution to the following problem:

$$f(\hat{w}, \sigma) = \arg\min_w \|w\|_\Lambda^2 + \gamma \|w - \hat{w}\|_1;$$ Equation (5);

Note that the first term of the cost function corresponds to the likelihood of w under Gaussian distribution, and the second term is the L−1 normed distance between w and the initial noise estimate ŵ. A simple proof is provided as follows. Let Δw = w − ŵ. We have:

$$\Delta w^* = \arg\min_{\Delta w} \|\Delta w + \hat{w}\|_\Lambda^2 + \gamma \|\Delta w\|_1;$$ Equation (6).

The solution to Equation 6 is well known as:

(7)

$$\Delta w_i^* = -\text{sign}(\hat{w}_i) \left( |\hat{w}_i| - \frac{\gamma \cdot \sigma_i}{2} \right)^+;$$ Equation (7);

where $(x)^+ = \max(x, 0)$. Therefore, $f(\hat{w}) = \Delta w^* + \hat{w}$, and hence:

$$f(\hat{w}_i) = \begin{cases} \hat{w}_i & \text{if } \hat{w}_i \leq \frac{\gamma \cdot \sigma_i}{2} \\ \text{sign}(\hat{w}_i) \frac{\gamma \cdot \sigma_i}{2} & \text{Otherwise} \end{cases};$$ Equation (8);

Note that there exists one-to-one mapping between α and γ, i.e. α = γ/2.

The above description is based on the noise estimation, it should be noted however, that the same approach can also be applied for the improvement of signal estimation. That is, starting from an initial estimate of the signal, and the signal statistics or prior knowledge, an update operator can be designed to modify and make it better follow the true signal x.

As alluded to, the blocks illustrated in FIG. 5 are performed in either projection space, or imaging space. Generally, the statistics of noise is better known in projection space, but noise itself is known better in image space. As such, to take advantage of this knowledge, according to an embodiment the noise is estimated in image space but the known statistical information regarding the noise is applied in projection space.

Figure 6:
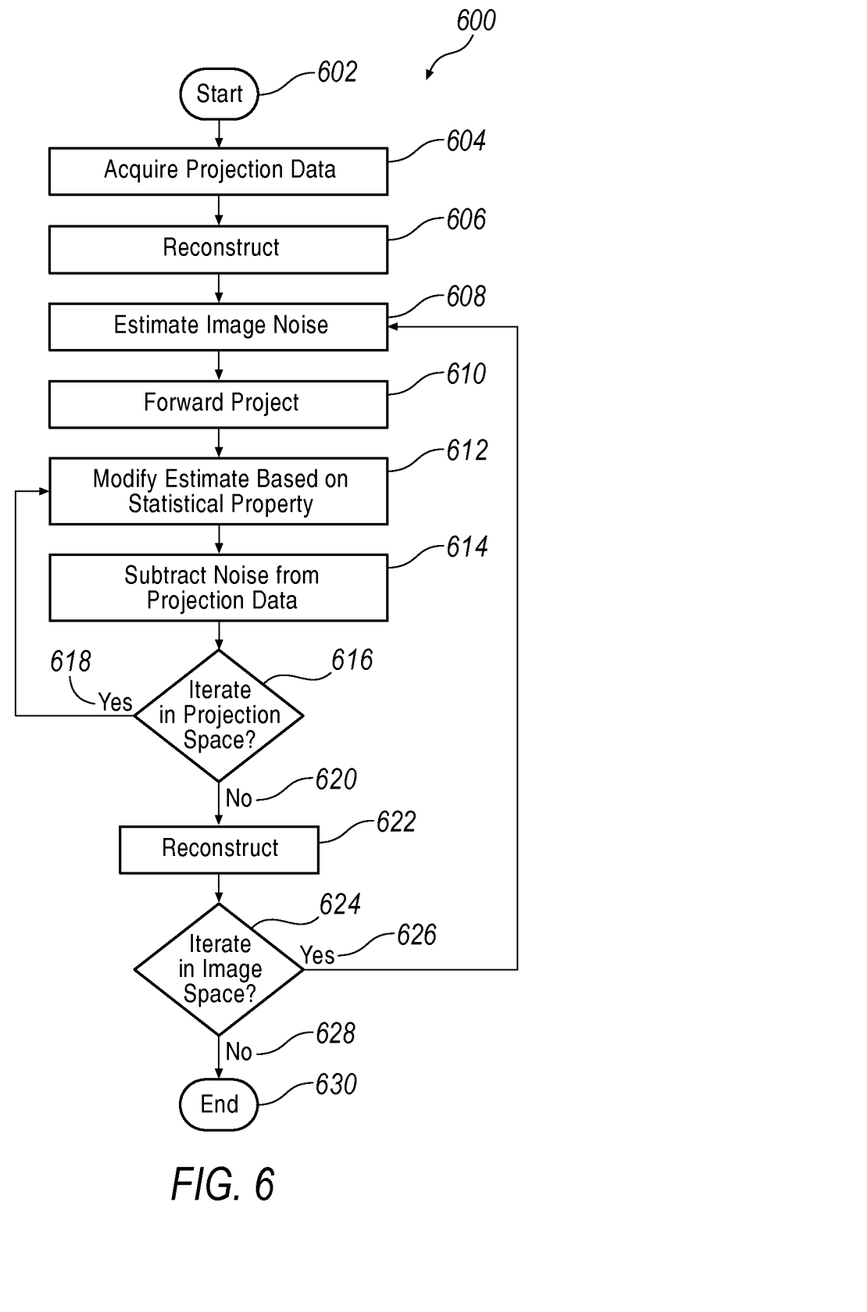
FIG. 6 is method of de-noising CT data according to one example.

Referring to FIG. 6, method or process flow 600 begins at step 602 and at step 604, CT projection data is acquired. An image is reconstructed 606 using a reconstruction process flow such as filtered back-projection (FBP), and using the originally acquired or obtained CT projection data. FBP is commonly known as an image reconstruction process that includes convolution of the measured projection with a reconstruction kernel, and the back-projection of a filtered projection. At step 608 an estimate of the image noise is conducted and, as stated above, the estimate at step 608 is conducted in image space. At step 610 the image noise is forward projected and into projection space, to generate an initial projection noise estimate. At step 612 the estimate of noise, again and still in projection space, is modified consistent with the above description, using a statistical property of noise in projection space. The noise is subtracted or removed from the original CT projection data at step 614, by subtracting the modified noise estimate therefrom to generate noise-removed projection data.

As also stated with respect to FIG. 5 above, after only the first pass through step 614, the image may be reconstructed. Or, iteration may be conducted in either the projection space or and/or the image space. That is, iterations may be performed to revise the noise-removed projection data by subsequently estimating the noise in image space based at least on reconstruction of the noise-removed projection data from a previous step. Or, iterations may be performed to revise the noise-removed projection data by subsequently modifying the estimated noise in projection space based at least on the noise-removed projection data from a previous step, and prior to reconstructing the final image. Thus, at step 616 if iterating 618 in projection space, then control returns to step 612. If not 620, then at step 622 and image is reconstructed, and at step 624, method 600 determines whether iterating in image space. If so 626, then control returns to step 608 and the process repeats therefrom. If not 628, then the process ends 630.

Because modification of the noise estimate in projection space is conducted based solely on the statistics of the noise, such operations are done without using image or projection data from neighboring pixels relative to the respective pixel having its noise removed.

Figure 7:
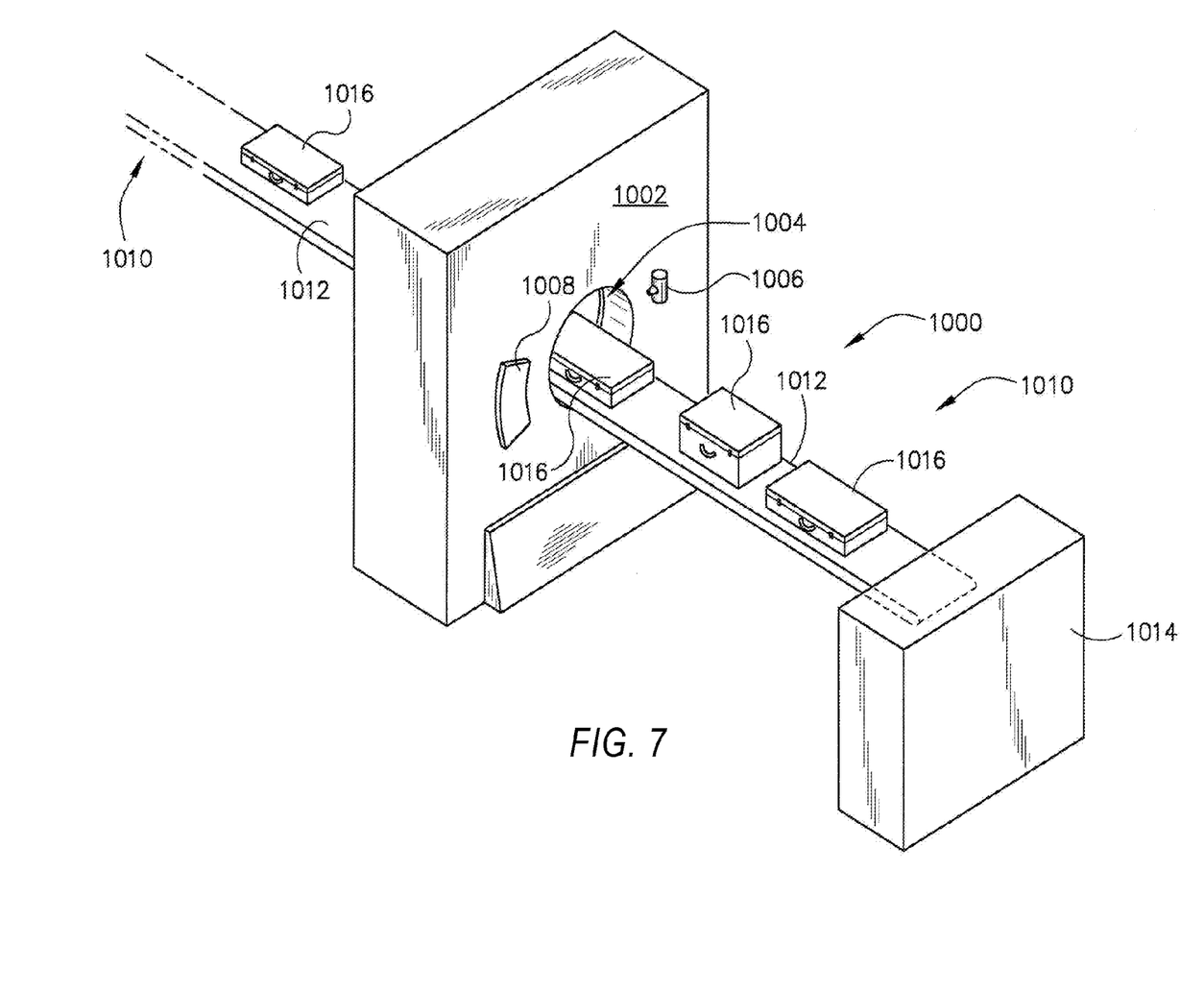
FIG. 7 is a pictorial view of a CT system for use with a non-invasive package inspection system.

Referring now to FIG. 7, there is shown a package/baggage inspection system 1000 that can use the image acquisition and reconstructions techniques according to embodiments disclosed and which includes a rotatable gantry 1002 having an opening 1004 therein through which packages or pieces of baggage may pass. The rotatable gantry 1002 houses one or more x-ray energy sources 1006 as well as a detector assembly 1008 having scintillator arrays comprised of scintillator cells. A conveyor system 1010 is also provided and includes a conveyor belt 1012 supported by structure 1014 to automatically and continuously pass packages or baggage pieces 1016 through opening 1004 to be scanned. Objects 1016 are passed through opening 1004 by conveyor belt 1012, imaging data is then acquired, and the conveyor belt 1012 removes the packages 1016 from opening 1004 in a controlled and continuous manner. As a result, postal inspectors, baggage handlers, and other security personnel may non-invasively inspect the contents of packages 1016 for explosives, knives, guns, contraband, etc.

An implementation of system 10 and/or 1000 in an example comprises a plurality of components such as one or more of electronic components, hardware components, and/or computer software components. A number of such components can be combined or divided in an implementation of the system 10 and/or 1000. An exemplary component of an implementation of the system 10 and/or 1000 employs and/or comprises a set and/or series of computer instructions written in or implemented with any of a number of programming languages, as will be appreciated by those skilled in the art. An implementation of system 10 and/or 1000 in an example comprises any (e.g., horizontal, oblique, or vertical) orientation, with the description and figures herein illustrating an exemplary orientation of an implementation of the system 10 and/or 1000, for explanatory purposes.

An implementation of system 10 and/or system 1000 in an example employs one or more computer readable signal bearing media. A computer-readable signal-bearing medium in an example stores software, firmware and/or assembly language for performing one or more portions of one or more implementations. An example of a computer-readable signal-bearing medium for an implementation of the system 10 and/or the system 1000 comprises the recordable data storage medium of the image reconstructor 34, and/or mass storage device 38 of computer 36. A computer-readable signal-bearing medium for an implementation of the system 10 and/or the system 1000 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 10 and/or the system 1000, for instance, one or more of a telephone network, a local area network ("LAN"), a wide area network ("WAN"), the Internet, and/or a wireless network.

According to one embodiment, an imaging system includes a computer programmed to reconstruct original CT projection data, estimate noise in image space, forward project the image noise estimate to generate an initial projection noise estimate, modify the initial projection noise estimate using a statistical property of noise in projection space, remove noise in the original CT projection data by subtracting the modified noise estimate therefrom to generate noise-removed projection data, and reconstruct a final image based on the noise-removed projection data.

According to another embodiment, a method of de-noising CT imaging data includes estimating noise in image space from reconstructed originally acquired CT projection data, modifying the estimated noise in projection space using a statistical property of noise in projection space, subtracting noise from the originally acquired CT projection data using the modified estimation of the noise to generate noise-removed projection data, and reconstructing a final image using the noise-removed projection data.

According to yet another embodiment, a computer readable storage medium having stored thereon a computer program comprising instructions, which, when executed by a computer, cause the computer to reconstruct originally acquired CT projection data, estimate noise in image space in the reconstructed data, forward project the image noise estimate to generate an initial projection noise estimate, modify the initial projection noise estimate using a statistical property of noise in projection space, remove noise in the originally acquired CT projection data by subtracting the modified noise estimate therefrom to generate noise-removed projection data, and reconstruct a final image based on the noise-removed projection data.

A technical contribution for the disclosed method and apparatus is that it provides for a computer-implemented apparatus and method of de-noising and restoring signals in computed tomography (CT) image data.

When introducing elements of various embodiments of the disclosed materials, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications).

While the disclosed materials have been described in detail in connection with only a limited number of embodiments, it should be readily understood that the embodiments are not limited to such disclosed embodiments. Rather, that disclosed can be modified to incorporate any number of variations, alterations, substitutions or equivalent arrangements not heretofore described, but which are commensurate with the spirit and scope of the disclosed materials. Furthermore, while single energy and dual-energy techniques are discussed above, that disclosed encompasses approaches with more than two energies. Additionally, while various embodiments have been described, it is to be understood that disclosed aspects may include only some of the described embodiments. Accordingly, that disclosed is not to be seen as limited by the foregoing description, but is only limited by the scope of the appended claims.

What is claimed is:

1. An imaging system comprising a computer programmed to execute stored routines which, when executed, causes acts to be performed comprising:
   reconstruct original computed tomography (CT) projection data;
   estimate noise in image space to generate an image noise estimate;
   forward project the image noise estimate to generate an initial projection noise estimate;
   modify the initial projection noise estimate using a statistical property of noise in projection space;
   remove noise in the original CT projection data by subtracting the modified noise estimate therefrom to generate noise-removed projection data; and
   reconstruct a final image based on the noise-removed projection data.

2. The imaging system of claim 1, wherein the computer is further programmed to modify the initial projection noise estimate without using image or projection data from neighboring pixels relative to the respective pixel having its noise removed.

3. The imaging system of claim 1, wherein the imaging system is a CT system.

4. The imaging system of claim 1, wherein the computer is further programmed to modify the initial projection noise using a non-decreasing function that is based on:
   A) a forward projection of the estimated noise in image space; and
   B) noise statistics that include a standard deviation in projection space.

5. The imaging system of claim 1, wherein the imaging system is a CT system that includes:
   a rotatable gantry for receiving an object to be scanned;
   a generator configured to energize an x-ray source to generate x-rays; and
   a detector positioned to receive the x-rays that pass through the object.

6. The imaging system of claim 1, wherein the computer is further programmed to iterate to revise the noise-removed projection data by being programmed to subsequently estimate the noise in image space based at least on the noise-removed projection data from a previous step, and prior to reconstructing the final image.

7. The imaging system of claim 1, wherein the computer is further programmed to iterate to revise the noise-removed projection data by being programmed to subsequently modify the estimated noise in projection space based at least on the noise-removed projection data from a previous step, and prior to reconstructing the final image.

8. A method of de-noising CT imaging data, comprising:
   estimating noise in image space from reconstructed originally acquired CT projection data;
   modifying the estimated noise in projection space using a statistical property of noise in projection space;
   subtracting noise from the originally acquired CT projection data using the modified estimation of the noise to generate noise-removed projection data; and
   reconstructing a final image using the noise-removed projection data.

9. The method of claim 8, further comprising forward projecting the noise estimated in image space to generate the initial estimation of the noise in projection space.

10. The method of claim 8, wherein the step of modifying the estimated noise in projection space is further conducted without using image or noise data from neighboring pixels relative to the respective pixel having its noise removed.

11. The method of claim 8, further comprising modifying the estimated noise in projection space using a non-decreasing function that is based on:
    A) a forward projection of the estimated noise in image space; and
    B) noise statistic that include a standard deviation in projection space.

12. The method of claim 8, further comprising iterating to revise the noise-removed projection data by subsequently estimating the noise in image space based at least on reconstruction of the noise-removed projection data from a previous step.

13. The imaging system of claim 8, further comprising iterating to revise the noise-removed projection data by subsequently estimating the noise in projection space, prior to reconstructing the final image, based at least on the noise-removed projection data from a previous step.

14. A non-transitory computer readable storage medium having stored thereon a computer program comprising instructions, which, when executed by a computer, cause the computer to:
    reconstruct originally acquired computed tomography (CT) projection data;
    estimate noise in image space in the reconstructed data;
    forward project the image noise estimate to generate an initial projection noise estimate;
    modify the initial projection noise estimate using a statistical property of noise in projection space;
    remove noise in the originally acquired CT projection data by subtracting the modified noise estimate therefrom to generate noise-removed projection data; and
    reconstruct a final image based on the noise-removed projection data.

15. The non-transitory computer readable storage medium of claim 14, wherein the instructions further cause the computer to modify the initial projection noise estimate without using image or noise data from neighboring pixels relative to the respective pixel having its noise removed.

16. The non-transitory computer readable storage medium of claim 14, wherein the instructions further cause the computer to acquire the originally acquired CT projection data in a CT system.

17. The non-transitory computer readable storage medium of claim 14, wherein the instructions further cause the computer to modify the initial projection noise using a non-decreasing function that is based on:
   A) a forward projection of the estimated noise in image space; and
   B) noise statistics that include a standard deviation in projection space.

18. The non-transitory computer readable storage medium of claim 14, wherein the CT projection data is data acquired from a CT system that includes:

a rotatable gantry for receiving an object to be scanned;
a generator configured to energize an x-ray source to generate x-rays; and
a detector positioned to receive the x-rays that pass through the object to generate the CT projection data therefrom.

19. The non-transitory computer readable storage medium of claim 14, wherein the instructions further cause the computer to revise the noise-removed projection data by being programmed to subsequently estimate the noise in image space based at least on reconstruction of the noise-removed projection data from a previous step.

20. The non-transitory computer readable storage medium of claim 1, wherein the instructions further cause the computer to iterate to revise the noise-removed projection data by being programmed to subsequently modify the estimated noise in projection space based at least on the noise-removed projection data from a previous step, and prior to reconstructing the final image.

* * * * *